United States Patent
Tanaka et al.

(10) Patent No.: US 7,722,584 B2
(45) Date of Patent: May 25, 2010

(54) AUTOMATIC URINE COLLECTION APPARATUS

(75) Inventors: Tetsuya Tanaka, Tokyo (JP); Ryosuke Miyagawa, Saitama (JP); Yoshikazu Ishitsuka, Ibaraki (JP); Hiroshi Koizumi, Tokyo (JP); Shigeharu Sayama, Fukuoka (JP)

(73) Assignee: Hitachi, Ltd., Tokyo (JP)

( * ) Notice: Subject to any disclaimer, the term of this patent is extended or adjusted under 35 U.S.C. 154(b) by 231 days.

(21) Appl. No.: 11/768,384

(22) Filed: Jun. 26, 2007

(65) Prior Publication Data

US 2008/0004576 A1 Jan. 3, 2008

(30) Foreign Application Priority Data

Jun. 28, 2006 (JP) ............................. 2006-178070

(51) Int. Cl.
 *A61M 1/00* (2006.01)
(52) U.S. Cl. ...................... 604/317; 604/318; 604/319; 604/320; 604/326; 604/327; 604/328; 604/329; 604/330; 604/331; 604/332; 604/346; 604/347; 604/348; 604/349; 604/350; 604/540
(58) Field of Classification Search ......... 604/317–320, 604/326–332, 346–350, 540
See application file for complete search history.

(56) References Cited

U.S. PATENT DOCUMENTS

| | | | | |
|---|---|---|---|---|
| 4,619,648 A | * | 10/1986 | Rath et al. ................... | 604/326 |
| 4,631,061 A | | 12/1986 | Martin | |
| D330,770 S | * | 11/1992 | Rodomista et al. ......... | D24/216 |
| D359,195 S | * | 6/1995 | Mukai et al. ................. | D7/309 |
| D359,357 S | * | 6/1995 | Bigler et al. ................ | D24/186 |
| 5,466,229 A | * | 11/1995 | Elson et al. ................. | 604/317 |
| D376,651 S | * | 12/1996 | Paloian ....................... | D24/216 |
| 5,736,098 A | * | 4/1998 | Kerwin et al. ................. | 422/28 |
| 5,891,051 A | * | 4/1999 | Han et al. .................... | 600/573 |
| 7,160,273 B2 | * | 1/2007 | Greter et al. ................ | 604/319 |
| D536,782 S | * | 2/2007 | Koizumi et al. ............ | D24/108 |
| D561,514 S | * | 2/2008 | Cortese et al. ............... | D7/309 |
| D564,655 S | * | 3/2008 | Koizumi et al. ............ | D24/108 |
| 7,438,706 B2 | * | 10/2008 | Koizumi et al. ............ | 604/327 |
| 2007/0010797 A1 | * | 1/2007 | Nishtala et al. ............. | 604/540 |

(Continued)

FOREIGN PATENT DOCUMENTS

DE 19619597 11/1997

(Continued)

OTHER PUBLICATIONS

European Search Report, EP 07012312, Oct. 15, 2007, 4 pages.

*Primary Examiner*—Tatyana Zalukaeva
*Assistant Examiner*—Ginger T Chapman
(74) *Attorney, Agent, or Firm*—Mattingly & Malur, P.C.

(57) ABSTRACT

An automatic urine collection apparatus includes a collection container for accumulating urine transferred from a urine receiver through a tube and a main body for supporting the collection container, wherein the main body includes a suction pump for sucking the urine received by the urine receiver and carrying the urine to the collection container, a mass sensor for measuring the urine accumulated in the collection container, a control board for calculating a volume of the urine based on the measured mass of the urine, and an indicator for indicating the calculated volume of the urine.

11 Claims, 5 Drawing Sheets

U.S. PATENT DOCUMENTS

2007/0219532 A1* 9/2007 Karpowicz et al. .......... 604/540

FOREIGN PATENT DOCUMENTS

| | | |
|---|---|---|
| EP | 1520567 | 4/2005 |
| EP | 1649838 | 4/2006 |
| JP | 2003-126242 | 5/2003 |
| JP | 2004-223112 | 8/2004 |
| JP | 2006-136491 | 6/2006 |

* cited by examiner

AUTOMATIC URINE COLLECTION APPARATUS

BACKGROUND OF THE INVENTION

1. Field of the Invention

The present invention relates to an automatic urine collection apparatus for automatically collecting urine excreted by such a bedridden patient and elderly person.

2. Description of the Related Art

Recently is known an automatic urine collection system for automatically collecting urine excreted by such a bedridden patient and elderly person. In general, the automatic urine collection system is mainly configured with a urine receiver attached to a private part of such a patient through a diaper; a tube of which one end is connected to the urine receiver; and an automatic urine collection apparatus connected to the other end of the tube. As the automatic urine collection apparatus is conventionally known the apparatus including a collection container for accumulating urine discharged from the urine receiver through the tube and a suction pump for sucking the urine accumulated in the urine receiver and carrying it to the collection container.

In such an automatic urine collection apparatus there has occurred a request of a user wanting to know a volume of urine accumulated in a collection container in order to make the volume an index for judging a health condition of a care receiver and a timing of disposing of the urine accumulated in the collection container.

As an invention to be able to cope with such a request is disclosed an apparatus for detecting a level of urine collected in a collection container (for example, see Japanese Patent Laid-Open Publication No. 2003-126242). The apparatus disclosed in the JP 2003-126242 is configured to float a float having a built-in permanent magnet in urine within a collection container and to detect the float ascending as the urine is accumulated by a magnetic sensor provided on an upper face of a lid part of the collection container.

However, the automatic urine collection apparatus disclosed in the JP 2003-126242 is configured to be able to detect the float when the float reaches the lid part of the collection container, and therefore, there is a problem that a urine level (volume of urine) can be measured only when the container is full of the urine.

Consequently, there is a need for an automatic urine collection apparatus that can measure a volume of urine regardless of the volume and that comprises a collection container easily washed.

SUMMARY OF THE INVENTION

The present invention is an automatic urine collection apparatus comprising a collection container for accumulating urine transferred from a urine receiver through a tube, and a main body for supporting the collection container; wherein the main body comprises a suction pump for sucking the urine received by the urine receiver and carrying the urine to the collection container, a mass sensor for measuring a mass of the urine accumulated in the collection container, a control board for calculating a volume of the urine based on the measured mass of the urine, and an indicator for indicating the calculated volume of the urine.

In accordance with the above automatic urine collection apparatus, it is possible to measure the mass of urine by using the mass sensor, and the collection container and the mass sensor can be separately configured.

In accordance with the present invention, the volume of urine can be measured regardless the volume by using the mass sensor, and the sensor does not touch the urine by separating the collection container and the mass sensor, and the collection container can be easily washed.

BRIEF DESCRIPTION OF THE DRAWINGS

FIG. 1A is an perspective view illustrating a state in use of the apparatus; and FIG. 1B is an exploded perspective view showing a state of a main body and collection container of the apparatus being disassembled.

BEST MODE FOR CARRYING OUT THE INVENTION

Here will be described a best mode (hereinafter referred to as "embodiment" for carrying out an automatic urine collection apparatus relating to the present invention in detail, referring to drawings as needed.

<Automatic Urine Collection System>

Figure 5:
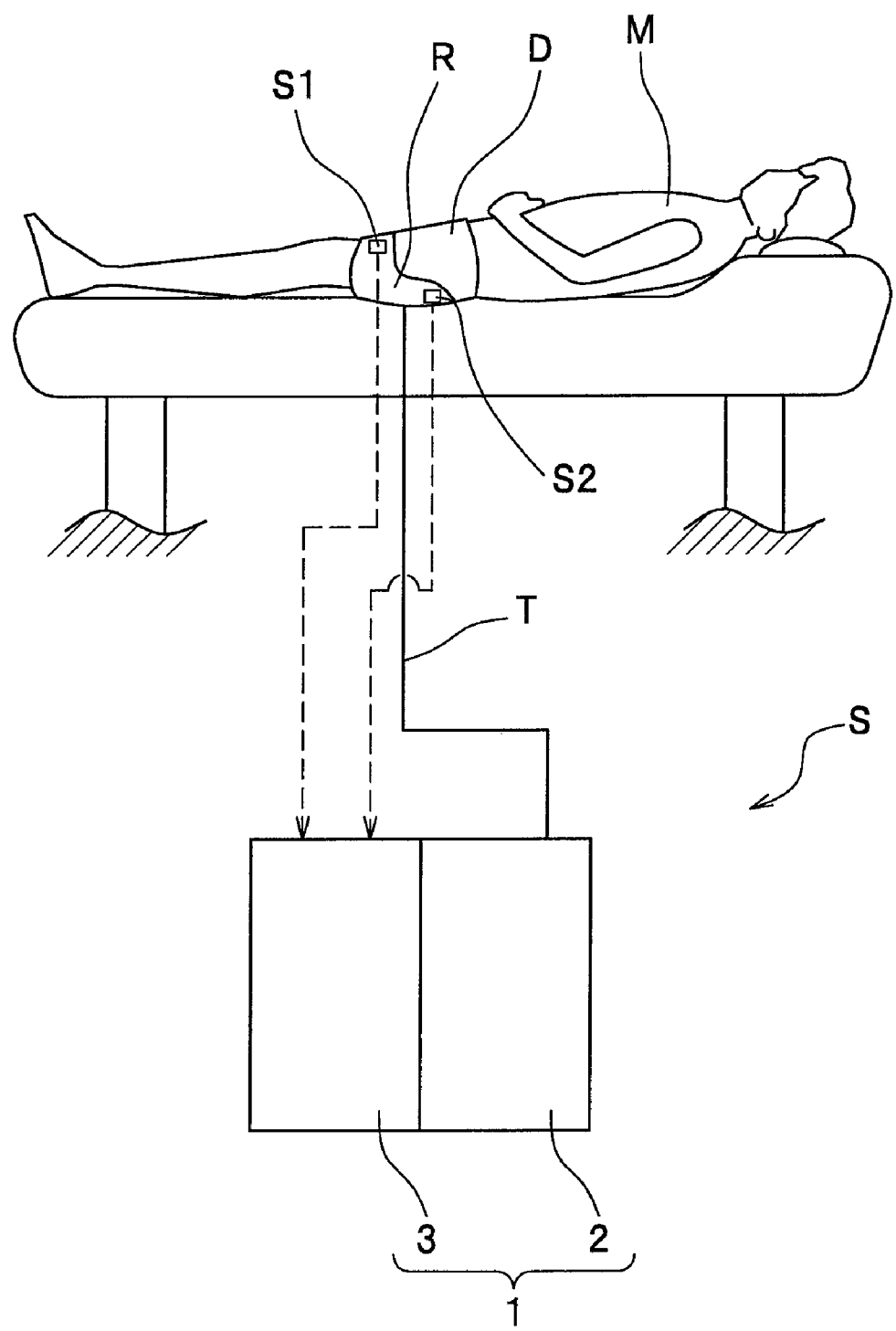
FIG. 5 is a configuration drawing showing an automatic urine collection system comprising the automatic urine collection apparatus of the embodiment.

As shown in FIG. 5, an automatic urine collection system S is mainly configured with a urine receiver R attached to a diaper (pad) D for temporary receiving urine excreted from a patient M (hereinafter referred to as "user" as needed), and an automatic urine collection apparatus 1 for automatically collecting the urine received by the urine receiver R through a tube T. Furthermore, within the diaper D are provided a urine sensor S1 for detecting the urine excreted from the patient M and a human waste sensor S2 for detecting human waste excreted from the patient M; signals detected by these sensors S1, S2 are adapted to be transmitted to the automatic urine collection apparatus 1. In addition, both the urine sensor S1 and the human waste sensor S2 are sensors for detecting moisture and are respectively used as the urine sensor S1 and the human waste sensor S2 by differentiating their placement positions.

In addition, although a silicone rubber and a vinyl chloride are generally used as a material of the tube T, the silicone rubber is preferable, considering an influence on an environment.

<<Automatic Urine Collection Apparatus>>

Figure 1A:
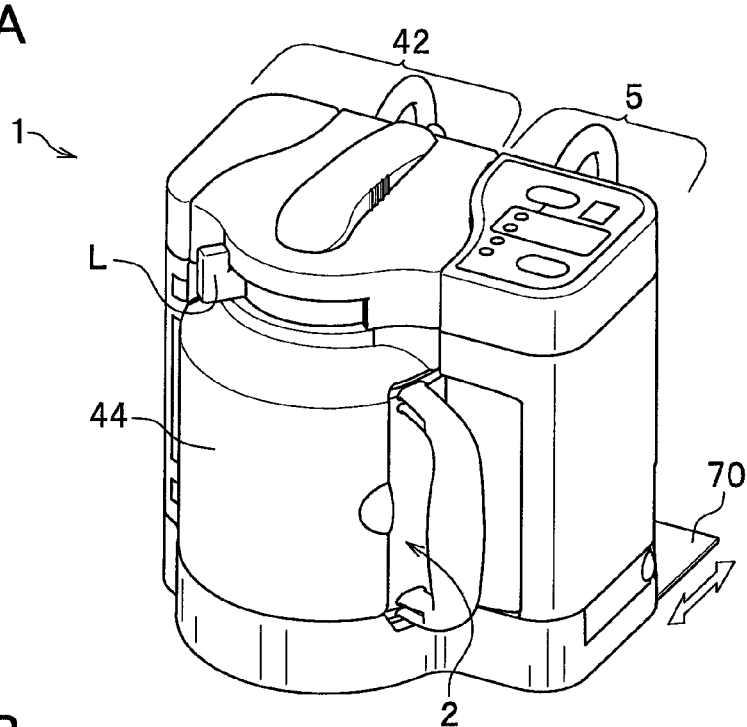
FIGS. 1A and 1B are drawings of an automatic urine collection apparatus relating to an embodiment of the present invention.
Figure 1B:
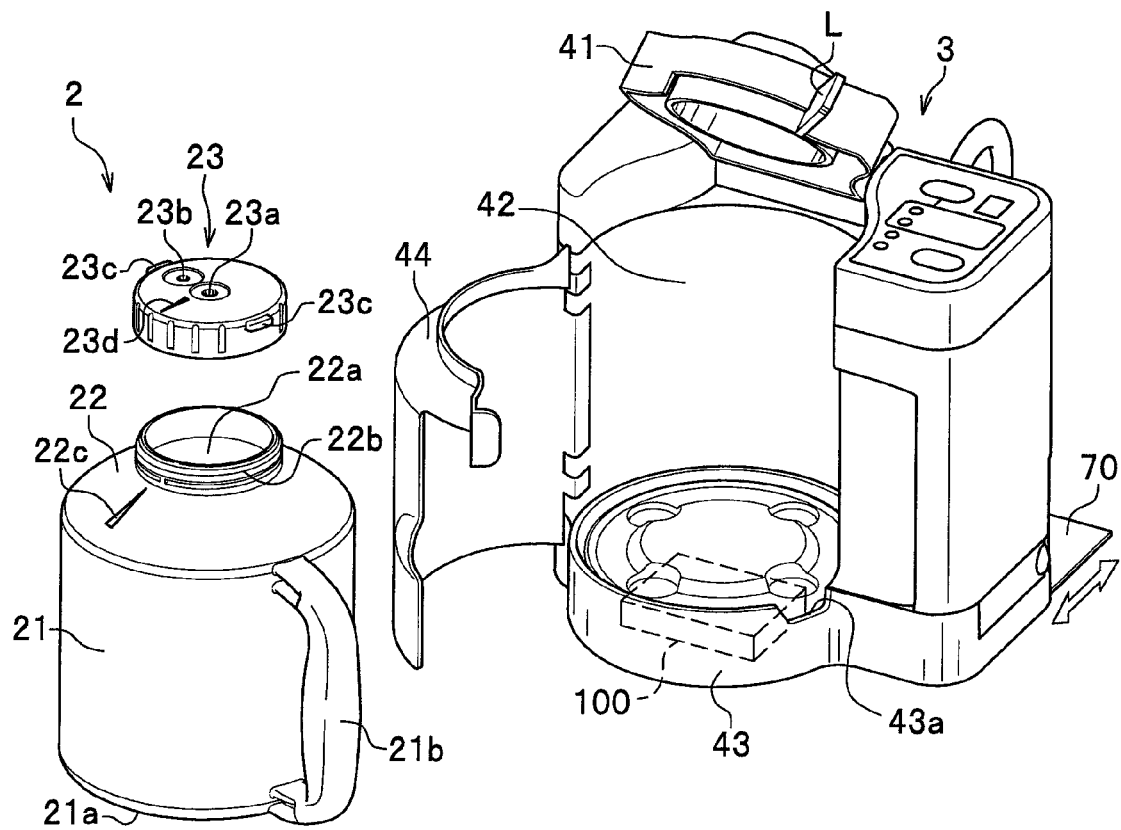

As shown in FIGS. 1A and 1B, the automatic urine collection apparatus 1 comprises a collection container 2 for accumulating urine transferred from the urine receiver R (see FIG. 5) through the tube T (see FIG. 5); and a main body 3 configured to mainly accommodate a suction pump 53 (see FIG. 2), and a mass sensor 100 for measuring a mass of the urine within the container 2, wherein the pump 53 sucks the urine received by the receiver R and carries the urine to the container 2.

<<Collection Container>>

As shown in FIG. 1B, the collection container 2 comprises an approximately cylindrical tank part 21 with a bottom having a predetermined depth, an upper face part 22 extendedly provided on top of the tank part 21, and a container lid 23 for sealing an opening 22a formed in the upper face part 22.

Because in the tank part 21 its inside is reduced in pressure by a suction action of the suction pump 53 (see FIG. 2), the part 21 is formed into the approximately cylindrical form with the bottom in order to obtain a predetermined strength. In the tank part 21 the thicker its diameter is and the lower its height is, the lower its center of gravity is; accordingly, the more stable the part 21 is and is difficult to fall down. A material of the tank part 21 preferably satisfies to simultaneously have a weight easy to carry and a predetermined strength, for example, like plastics represented by polycarbonate and polypropylene.

Furthermore, the tank part 21 is preferably a transparent member so that a user can easily grasp a volume of urine (hereinafter referred to as "urine volume" as needed) accumulated within the part 21. Moreover, when the tank part 21 is made translucent not transparent, it is possible to pay attention to a user privacy although the volume of the urine is seeable by eyes from an outside of the collection container 2. Moreover, by configuring the tank part 21 with a transparent (or translucent) member, it is possible to check what degree the collection container 2 may be tilted in disposing of the urine.

In addition, in an in-use state of the automatic urine collection apparatus 1 shown in FIG. 1A, paying attention to a user privacy, the collection container 2 is configured not to be seeable by providing a tank cover 44. In the automatic urine collection apparatus 1 in such a state, the mass sensor 100 for measuring a volume of urine plays an important role.

While a bottom face 21a of the tank part 21 comprises one horizontal face so as to be able to be placed on a floor when the collection container 2 is detached from the main body 3, an outer peripheral edge of the face 21a comprises a spherical face and a tilt face in order to obtain a strength coping with a pressure reduction. Furthermore, on a side face of the tank part 21 is formed a handgrip 21b for assisting carry by a user. The handgrip 21b is also utilized for positioning the collection container 2 in accommodating the container 2 in the main body 3.

The upper face part 22 is a member like an approximately semi-sphere making a center thereof an apex and provided on top of the tank part 21; on the top (apex portion) of the part 22 is formed the opening 22a sealed by the container lid 23. Thus by forming the upper face part 22 not as a flat face but like the approximately semi-sphere having a predetermined angle, it is possible to dispose of urine from the opening 22a even if a tilting angle of the tank part 21 is small.

In addition, although the upper face part 22 is preferable to be integrally molded with the tank part 21, they may be separately molded and then connected.

The opening 22a is formed to be smaller than a diameter of the tank part 21. Thus configured, it is possible to prevent urine from spilling outside in such carrying the collection container 2 in a full level of the urine. Moreover, it is possible to form a packing 232 (see FIG. 2) for pushing the container lid 23 to be smaller. Moreover, because pushing nonuniformity in pushing the packing 232 becomes less, a pressure inside the collection container 2 is more easily reduced by the suction pump 53.

Furthermore, a thread part 22b raised up along a rim of the opening 22a has a male thread that can be screwed together with a female thread (not shown) on an inner periphery of the container lid 23.

The container lid 23 is a cylindrical member with a roof for sealing the opening 22a of the collection container 2; on the inner periphery of the lid 23 is formed the female thread (not shown) screwed together with the male thread of the thread part 22b provided at the opening 22a of the container 2.

A positioning line 22c and a positioning line 23d respectively indicated in radial directions on the upper face part 22 and the container lid 23 are targets to make constant a relative angle between the collection container 2 and the lid 23; when the thread of the container lid 23 is fully closed, the lines 22c and 23d are normally positioned in alignment with each other.

On an upper face of the container lid 23 are formed an introduction inlet 23a for communicating with the tube T and introducing urine into the collection container 2; and a suction inlet 23b for communicating with the suction pump 53 and sucking air within the container 2.

Furthermore, at opposing positions of an outer periphery of the container lid 23 are protrudingly provided engagement claws 23c for coupling the lid 23 with a main body lid 41 of the main body 3.

Figure 2:
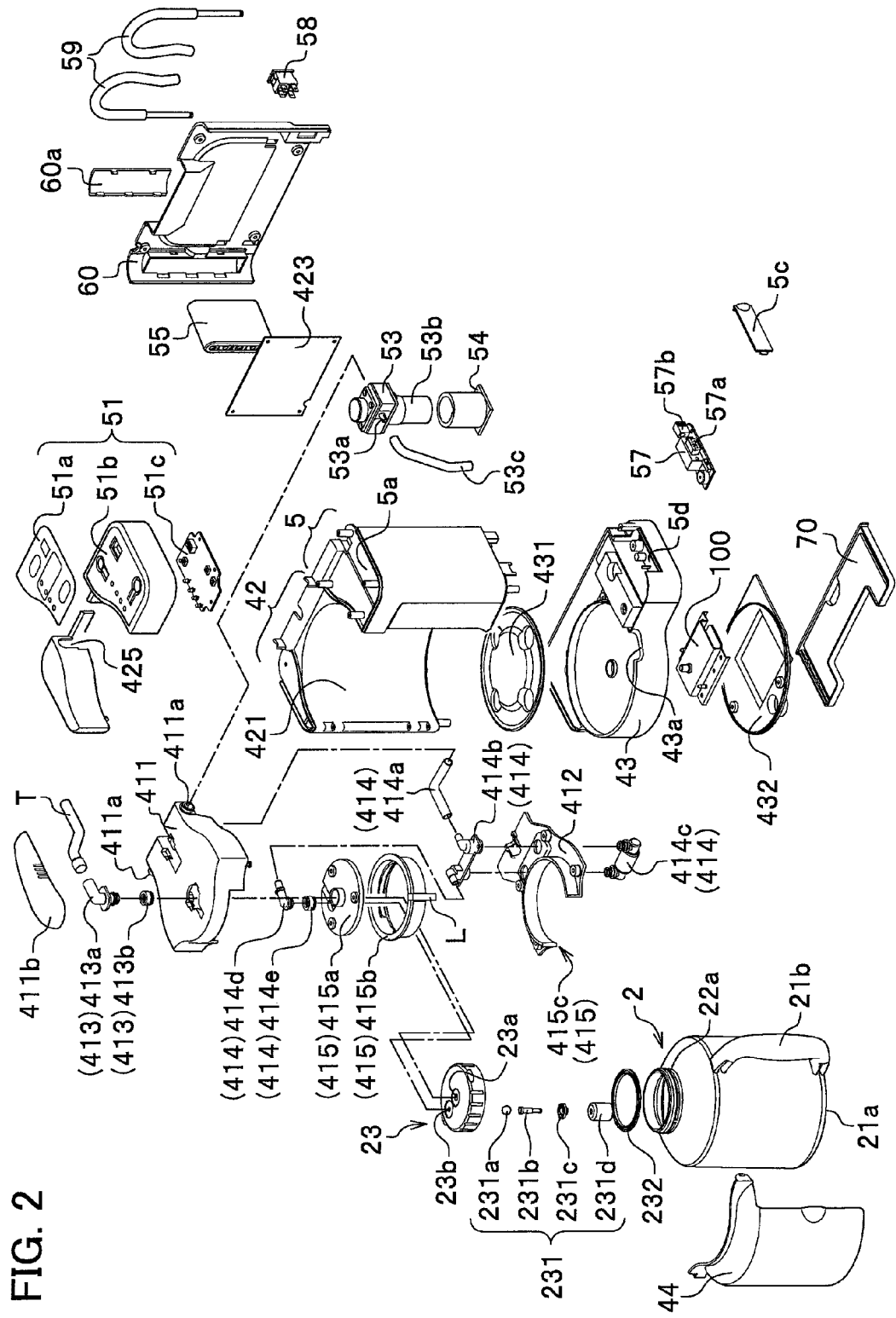
FIG. 2 is an exploded perspective view showing components of the automatic urine collection apparatus of the embodiment.
Figure 3:
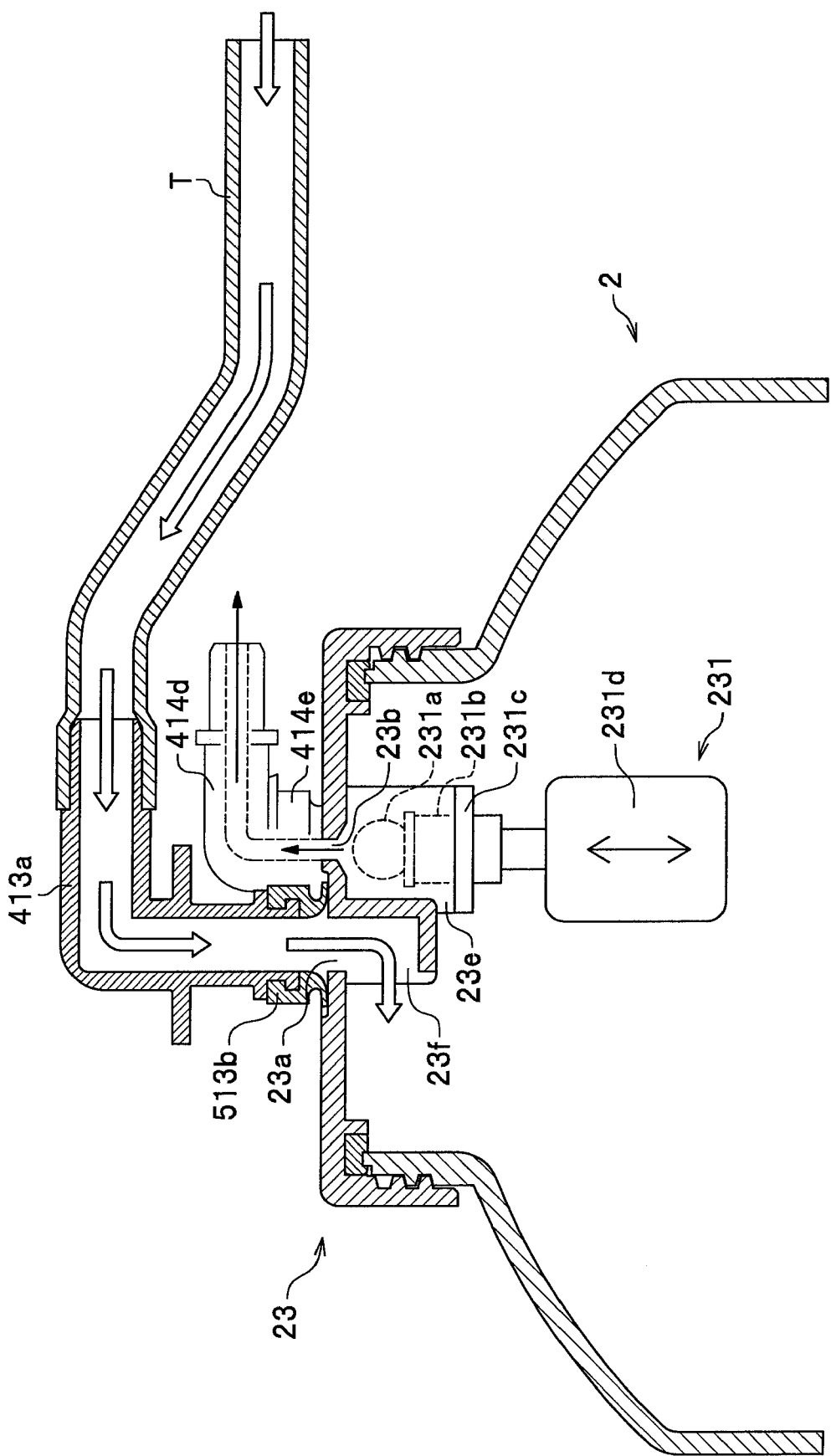
FIG. 3 is a vertical section drawing illustrating a configuration of a container lid of the collection container of the embodiment.

As shown in FIGS. 2 and 3, below the suction inlet 23b is provided a suction stop means 231 for stopping suction when urine within the collection container 2 becomes full. The suction stop means 231 comprises, for example, a ball valve part 231a configured to directly seal the suction inlet 23b; a ball-valve-part support part 231b configured to include a bar-like member, of which an upper end is formed like a tray, and to support the ball valve part 231a at the upper end; an accommodation-part bottom lid 231c configured to hold a halfway of the support part 231b so as to be freely movable up and down; a float part 231d configured to be connected to a lower end of the support part 231b and to move up and down together with a fluctuation of a urine level; and an accommodation part 23e configured to include a space for the ball valve part 231a moving up and down therein. In addition, in any one of the accommodation-part bottom lid 231c and the accommodation part 23e is formed a hole not shown, and the suction inlet 23b and the inside of the collection container 2 are communicated.

In accordance with such the suction stop means 231, if a urine level becomes a full level, the float part 231d is pushed upward, and the ball valve part 231a seals the suction inlet 23b from its underside through the ball-valve-part support part 231b. In other words, in the full level of urine the suction is not further performed, and therefore, it is possible to stop introducing urine into the collection container 2. In other words, because it is possible in the full level of urine to prevent the urine from being sucked from the suction inlet 23b, it is possible to reduce a possibility that the suction pump 53 is contaminated with the urine and deteriorated in its function.

As shown in FIG. 3, a scattering-prevention member 23f is provided to block off a space between the introduction inlet 23a and a urine surface, and is hung down from the container lid 23. In accordance with such the scattering-prevention member 23f, when urine is discharged into the collection container 2 through the introduction inlet 23a from the tube T, it is possible to reduce scattering of the urine by restricting a flow rate of the urine dropping down and by dispersing a volume of the urine dropping at one place. Accordingly, because it is possible to prevent the container lid 23 from being contaminated, it is possible to reduce a labor hour of washing the lid 23. Furthermore, because it is possible to prevent the scattered urine from being sucked from the suction inlet 23b, it is possible to reduce a possibility that the suction pump 53 is contaminated with the urine and deteriorated in its function.

<<Main Body>>

As shown in FIGS. 1A and 1B, the main body 3 is integrally formed with: the main body lid 41 freely openable and closable and comprising a urine flow passage 413 and an air flow passage 414 (see FIG. 2); a container support part 42 comprising a semi-cylindrical accommodation-concave portion for accommodating the collection container 2; a bottom part 43 comprising the mass sensor 100 and where the container 2 is placed; the tank cover 44 for covering the container 2, paying attention to a user privacy; and an approximately columnar pump storage part 5 mainly comprising the suction pump 53 therein.

[Main Body Lid]

As shown in FIG. 2, the main body lid 41 mainly comprises, in its upper frame 411 and lower frame 412 of a base portion, the urine flow passage 413 connectable to the introduction inlet 23a of the container lid 23; the air flow passage 414 connectable to the suction inlet 23b of the lid 23; and a container-lid coupling mechanism 415 for coupling the lid 23.

When the freely-openable-and-closable main body lid 41 is in a closed state, connection ends of the urine flow passage 413 and the air flow passage 414 are configured to be respectively connected to the introduction inlet 23a and the suction inlet 23b; when the main body lid 41 is in an opened state, the connection ends of the passages 413 and 414 are configured to be respectively separated from the inlets 23a and 23b.

Hereinafter, if not otherwise described, a description will be made in the assumption that, as shown in FIG. 1A, the collection container 2 is accommodated in the main body 3 and the main body lid 41 is in the closed state.

The upper frame 411 configures a flat-plate-like upper wall and sidewall of the main body lid 41, and in the frame 411 a rim is configured to be formed downward from an edge of the upper wall across an approximately whole periphery. A size of the upper frame 411 in a plan view is slightly larger than that of the container lid 23, and an outer periphery portion of the lid 23 is positioned more inside than the edge of the frame 411.

Rotation shafts 411a, 411a formed at a back face side of the upper frame 411 are free-turnably placed in rotation shaft grooves 425, 425 of the container support part 42, and realize to open and close the main body lid 41.

Then a rotation shaft 411a at a side of the pump storage part 5 is configured to be hollow so that one end of an L-shaped pipe 414a can be exposed.

Furthermore, at middle of the back face side of the upper frame 411 is formed an accommodation-concave portion for the tube T. By disposing the tube T at the accommodation-concave portion, it is possible to prevent the tube T from being pressed by an edge at the back face side of the upper frame 411 in respectively opening and closing the main body lid 41.

The lower frame 412 configures a lower wall of the main body lid 41, is formed with a form basically corresponding to the upper frame 411, and at middle, has a turning-body support part 415c as the container lid coupling mechanism 415. At a front portion of the turning-body support part 415c is provided a notch matching with an operation range of a lever L protrudingly provided from a turning body 415b, and the lower frame 412 as a whole is configured to be approximately C-shaped.

The urine flow passage 413 comprises an introduction pipe 413a of which one end is connected to the tube T; and a rubber member 413b for sealing a space between the pipe 413a and the introduction inlet 23a of the container lid 23 without a gap in connecting the other end of the pipe 413a to the inlet 23a. The other end of the introduction pipe 413a and the rubber member 413b are connection ends in connecting the urine flow passage 413 to the container lid 23.

In addition, although the tube T and the introduction pipe 413a are connected at an upper side of the main body lid 41, the connection end of the urine flow passage 413 is configured to be exposed to an underside of the lid part 41 by passing the pipe 413a through the upper frame 411 and a through hole formed at middle of a shaft disc 415a.

In addition, in a measurement by the mass sensor 100, when the tube T disposed above is pulled, for example, by being unintentionally pulled or by an article being put on the tube T, there is a possibility that an upward force acts on the main body lid 41 and that a large error occurs in a measured value by the sensor 100.

Consequently, on top of the main body lid 41 is provided a tube cover 411b for fixing the tube T near the rotation shafts 411a. In accordance with such the tube cover 411b, when the tube T is pulled, because the rotation shafts 411a can receive a greater part of the pull force, it is possible to prevent the upward force from acting on the main body lid 41. In other words, regardless of the tube T being pulled or not pulled, it is possible to obtain a stable measurement value. Furthermore, in accordance with the tube cover 411b, it is possible to stably ensure the urine flow passage 413 without the tube T being entwined and folded.

In addition, a place where the tube T is fixed by the tube cover 411b is not specifically limited if it can reduce an upward force acting on the main body lid 41; however, the place is preferably on or near any one of the rotation shafts 411a.

The air flow passage 414 comprises an L-shaped pipe 414a; flow-passage forming members 414b, 414d; a liquid accumulation part 414c; and a rubber member 414e. In addition, as shown in FIG. 2, in the flow-passage forming member 414b are integrally formed a downstream portion for communicating the L-shaped pipe 414a and the liquid accumulation part 414c, and an upstream portion for communicating the flow-passage forming member 414d and the liquid accumulation part 414c. Furthermore, the liquid accumulation part 414c is provided so that urine does not reach the suction pump 53 by accumulating the urine when the urine flows in from a connection end of the air flow passage 414. The rubber member 414e seals without a gap a space between the flow-passage forming member 414d and the suction inlet 23b of the container lid 23 in connecting one end of the member 414d to the inlet 23b.

Then the air flow passage 414 is configured by sequentially connecting the L-shaped pipe 414a of which one end is connected through the suction pump 53 and a communication pipe not shown; the downstream portion of the flow-passage forming member 414b; the liquid accumulation part 414c; the upstream portion of the flow-passage forming member 414d; and the rubber member 414e. One end of the flow-passage forming member 414d and the rubber member 414e are connection ends in connecting the air flow passage 414 to the container lid 23.

In addition, although the air flow passage 414 is basically formed inside the main body lid 41, the connection end of the passage 414 is configured to be exposed to the underside of the lid part 41 by passing the flow-passage forming member 414d through the through hole formed in the shaft disc 415a.

Furthermore, the liquid accumulation part 414c is configured to be freely attachable and detachable from an underside of the lower frame 412, and thereby when urine is accumulated in the part 414c, it is possible to detach the part 414c and to dispose of the urine. Furthermore, the liquid accumulation part 414c is preferably configured with a transparent member so that a user can easily judge a state of a urine accumulation.

By coupling the main body lid 41 and the container lid 23, the container lid coupling mechanism 415 connects the urine flow passage 413 and the air flow passage 414 formed in the lid part 41 to the introduction inlet 23a and the suction inlet 23b formed in the lid 23, respectively.

The container lid coupling mechanism 415 comprises the shaft disc 415a fixed at middle of the upper frame 411 from the underside of the frame 411; the turning body 415b having an inner wall matching with an outer periphery of the disc 415a; and the turning body support part 415c having an inner wall matching with an outer periphery of the body 415b.

Then an upper portion of an inner periphery face of the turning body 415b fits outside the shaft disc 415a, and the body 415b is turnably supported thereon. Furthermore, on a lower portion of the inner periphery face of the turning body 415b is formed a not-shown thread screwed together with the engagement claws 23c of the container lid 23.

Moreover, an outer periphery face of the turning body 415b fits in the turning body support part 415c. On an upper periphery edge of the turning body 415b is formed a flange, and the body 415b is free-slidably supported at the turning body support part 415c.

Furthermore, on the outer periphery face of the turning body 415b is integrally provided the lever L for a user to turn the body 415b.

In the container lid coupling mechanism 415 thus configured, if a user turns the turning body 415b in a predetermined direction through the lever L (turning from right to left by about 45 degrees in FIG. 1A), the engagement claws 23c of the container lid 23 are put in a not-shown thread on the inner periphery face of the body 415b, and the collection container 2 is coupled with the main body lid 41. According to this coupling, because the rubber members 413b, 414e of the urine flow passage 413 and the air flow passage 414 are more elastically deformed, it is possible to more closely connect the connection ends of the urine flow passage 413 and the air flow passage 414 to the introduction inlet 23a and suction inlet 23b of the container lid 23, respectively.

[Container Support Part]

The container support part 42 comprises the semi-cylindrical accommodation-concave portion for accommodating the collection container 2. A vertical wall part 421 that is a sidewall on a side of the accommodation-concave portion is formed along a side face form of the collection container 2 in order to prevent it from falling down when it becomes an imbalance. In a normal state, between the collection container 2 and the vertical wall part 421, there is a gap to such an extent that direct contact is not made, so as not to influence a measurement by the mass sensor 100.

Furthermore, inside the container support part 42 are stored a control board 423 and a battery 55.

The control board 423 controls various instruments based on signals transmitted from the mass sensor 100, an indicator part 51, the urine sensor S1, and the human waste sensor S2. For example, the control board 423 is electrically connected to the urine sensor S1, the human waste sensor S2, the suction pump 53, the mass sensor 100, the indicator part 51, the battery 55, a power source switch 58, a terminal 57a, a terminal 57b, and the like.

The control board 423 comprises a CPU (Central Processing Unit), an involatile memory such as a ROM (Read Only Memory), and a volatile memory; in the involatile memory are stored a program and data requested for each control. Then it is assumed that the CPU reads a program into the memories, performs a calculation processing, and thereby each processing is realized.

In the volatile memory are recorded a volume of urine and the like measured by the mass sensor 100. In the volatile memory can be memorized an automatic urine collection apparatus ID (Identification), a user name, a user ID, a volume of urine before an operation of the suction pump 53, a volume of urine after the operation of the suction pump 53, and the like associated with each other.

The battery 55 is detachably stored in the container support part 42, and an opening of a battery storage part not shown is covered with a battery cover 60a. The battery 55 can supply its power to the suction pump 53, the indicator part 51, and the mass sensor 100 electrically connected through the control board 423. In addition, charging the battery 55 can also be performed by using an AC adaptor electrically connected through the terminal 57b.

[Bottom Part]

The bottom part 43 is a form corresponding to that of the bottom face 21a of the collection container 2, and it can be stably placed thereon. On the upper edge of the bottom part 43 is formed the accommodation-concave portion 43a corresponding to the handgrip 21b of the collection container 2, and thus a placement position of the container 2 is adapted to be automatically determined.

Furthermore, on the bottom part 43 is placed the mass sensor 100 for measuring a mass of the collection container 2 placed thereon. In FIG. 2 a main body of the mass sensor 100 is fixed so as to be embedded in a notch portion formed at middle of a bottom plate 432, and a sensor portion of the sensor 100 is exposed upward from a hole formed at middle of the bottom part 43.

In addition, the mass sensor 100 is not specifically limited if it can measure the mass of the collection container 2 placed on the bottom part 43; it is possible to use the mass sensor 100 conventionally known, for example, such as a static capacitance type, a spring type, a scale type, a load cell type, a tuning-fork vibration type, a string vibration type, a gyro type, an electromagnetic force balance type, and a magnetostriction type.

Furthermore, according to the type of the mass sensor 100, a tray 431 can be used as needed. For example, the tray 431 is used for equally distributing a load of the collection container 2 and transmitting it to the mass sensor 100. In addition, in a case of using the tray 431, its form is preferably associated with the bottom face 21a of the collection container 2.

[Tank Cover]

The tank cover 44 is comprised of an opaque member and covers the transparent (or translucent) collection container 2, paying attention to a user privacy. In the tank cover 44 an escape portion is formed at a portion corresponding to the handgrip 21b of the collection container 2.

[Pump Storage Part]

In the pump storage part 5 is mainly stored the suction pump 53.

The suction pump 53 is not specifically limited if it can suck air, and for example, a rotary pump is applicable. The rotary pump rotates a pair of rotors, thereby sucks air within the collection container 2, and has characteristics of bringing out a larger suction force in small size and of a drive noise being small.

In the suction pump 53 a suction inlet not shown is connected to a communication pipe not shown through a rubber (elastic member), and the pipe is connected to the L-shaped pipe 414a exposed from the rotation shaft 411a of the upper frame 411. Furthermore, a discharge outlet 53a of the suction pump 53 is communicated with a bottom portion of the automatic urine collection apparatus 1 through an approximately L-shaped pipe 53c.

Furthermore, a motor 53b under the suction pump 53 is joined to a sidewall of the pump storage part 5 through a rubber-like vibration absorber (elastic member) 54. Therefore, a noise and a vibration generated from the suction pump 53 can be absorbed mainly by the vibration absorber 54.

Moreover, in the pump storage part 5 its upper portion is formed as an attachment part 5a for attaching the indicator part 51; a lower portion of the part 5 is formed as a terminal accommodation part 5d for accommodating an external terminal 57.

Figure 4:
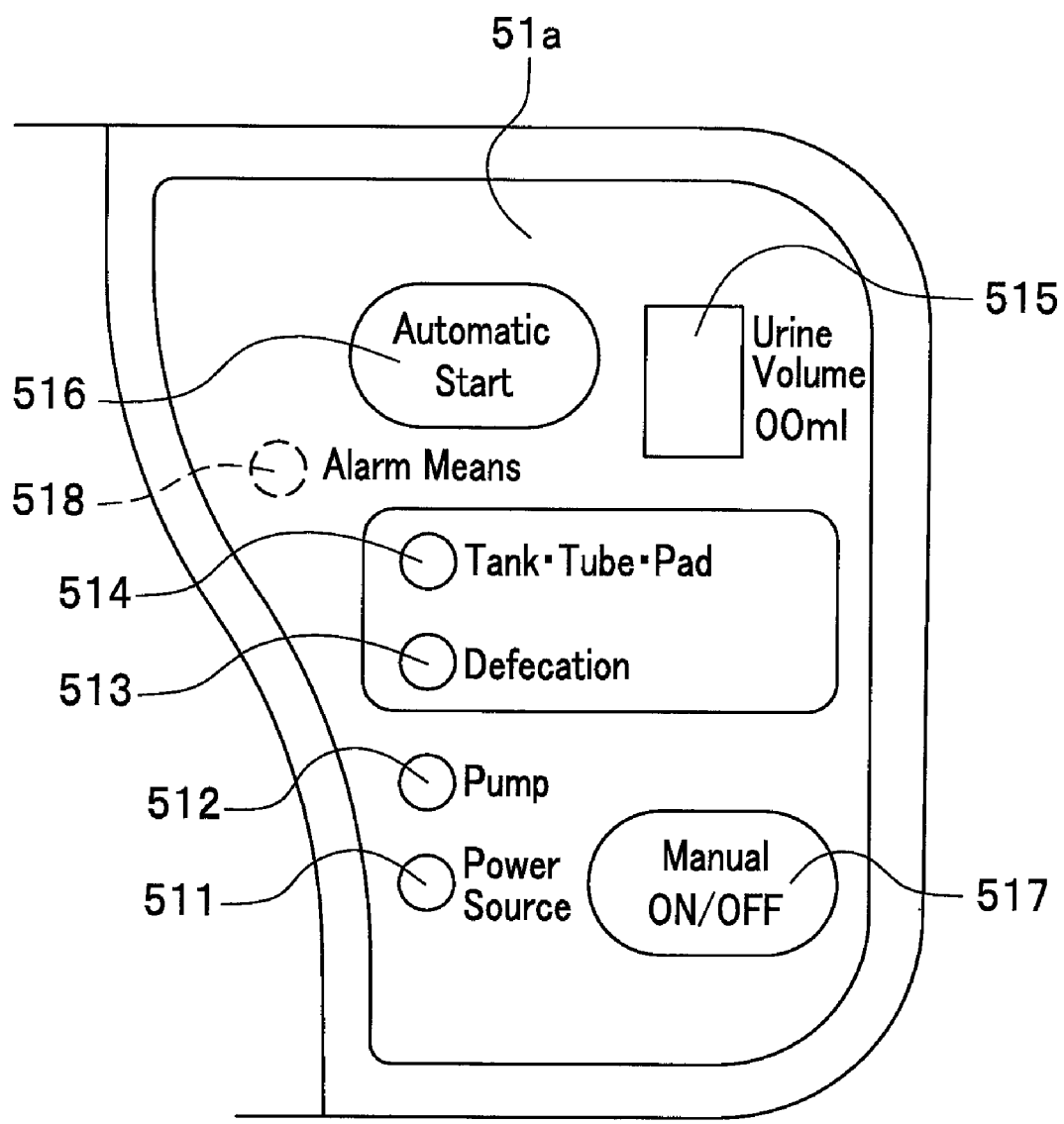
FIG. 4 is a plan view showing an operation panel of the automatic urine collection apparatus of the embodiment.

The indicator part 51 comprises an operation panel 51a, a switch escape part 51b, and a switch board 51c. As shown in FIG. 4, the operation panel 51a, on a surface of which characters are provided as needed, is a seal-like member and is configured to be pasted on an upper face of the switch escape part 51b. On the switch board 51c are provided switches corresponding to the characters provided as needed on the operation panel 51a, an indication window, lamps, and the like; the switch escape part 51b comprises an escape portion for indicating them.

As shown in FIG. 4, the operation panel 51a of the indicator part 51 relating to the embodiment specifically comprises a lamp 511 for indicating ON and OFF of a power source; a lamp 512 for indicating an operation state of the suction pump 53; a lamp 513 for indicating an operation state of the human waste sensor S2; a lamp 514 for indicating an operation state of the urine sensor S1; an indication window 515 for indicating a volume of urine within the collection container 2 measured; an automatic drive switch 516 for driving the motor 53b of the pump 53 by automatic control; and a manual drive switch 517 for manually driving the motor 53b.

The indication window 515 is preferably digital display so that a user can easily judge a volume of urine. Furthermore, the indication window 515 is practically sufficient if it is marked out and indicated for every 100 ml. For example, the indication window 515 is indicated by 11 levels of 1 to 10 in a case of an effective volume of the collection container 2 being one liter. Furthermore, in a case of the collection container 2 not being accommodated in the main body 3, "– (minus)" is indicated on the indication window 515.

Furthermore, in a case of a volume of urine nearing a full level (for example, not less than 600 ml for the full volume of one liter), the indication window 515 may also be configured to arouse a user's attention by flickering the digital display.

These controls can be easily performed by the control board 423 electrically connected to the indicator part 51 and the mass sensor 100.

The external terminal 57 comprises the terminal 57a for outputting such data of a volume of urine recorded in a volatile memory to such a personal computer and a printer, and the terminal 57b for connecting an AC adaptor thereto; and these are placed in the terminal accommodation part 5d formed under the pump storage part 5. Furthermore, in a case of not using the external terminal 57, the pump accommodation part 5d is closed by a cover 5c.

Hooks 59, 59 are used for hanging the automatic urine collection apparatus 1 on any one of a bed, a wheelchair, and the like, and each hook 59 is free-turnably placed on a back plate 60 of the main body 3. Specifically, the hook 59 is curved like a U letter; is hooked on a pipe of a bed, a wheelchair, and the like by the curved portion; and one end of the hook 59 is free-turnably placed in a horizontal direction. Thus the hook 59 is free-turnably placed, and thereby, even in a case of a pipe thickness of a bed, a wheelchair, and the like being different, it is possible to make the automatic urine collection apparatus 1 horizontal and to hook it on the pipe by adjusting a turning angle of the hook 59. Moreover, it is possible to adjust the automatic urine collection apparatus 1 to be horizontal by placing a spacer (not shown), of which a thickness is variable, under the back plate 60.

A falling-down-prevention plate 70 prevents the automatic urine collection apparatus 1 from falling down, and a flat plate having the approximately same form as that of a bottom face of the main body 3 is attached slidably with respect to the bottom face. When using the falling-down-prevention plate 70, an area of a bottom face of the automatic urine collection apparatus 1 is enlarged by pulling out the plate 70 toward a back of the apparatus 1; in a case of not using the plate 70, it is held so as to be stacked on the bottom face of the apparatus 1 by pushing the plate 70 toward a front of the apparatus 1. In addition, any form and size of the falling-down-prevention plate 70 are available if they can reduce a falling-down frequency of the automatic urine collection apparatus 1; they are not limited to the above.

<Operation of Automatic Urine Collection Apparatus>

Next will be described an operation of the automatic urine collection apparatus 1 relating to the embodiment.

In using the automatic urine collection apparatus 1, a user firstly places the collection container 2 locked with the container lid 23 on the bottom part 43 of the main body 3, and closes the main body lid 41. At this time the container lid 23 is positioned inside the turning body 415b.

Then if the user operates the lever L of the main body lid 41 and turns the turning body 415b, the engagement claws 23c of the container lid 23 and the inner thread of the turning body 415b are screwed together, and thus the lid 23 and the lid part 41 are coupled. At this time the connection ends of the urine flow passage 413 and the air flow passage 414 in the main body lid 41 are closely connected to the introduction inlet 23a and suction inlet 23b of the container lid 23, respectively, and are adapted to be communicated with the inside of the collection container 2. In such a state, the mass sensor 100 measures a combined mass of the collection container 2 and the main body lid 41; in a case of there being not urine yet in the collection container 2, the control board 423 makes the indicator part 51 indicate a mass (initial value) at this time as "0 (ml)."

Furthermore, in a state of the collection container 2 being not accommodated in the main body 3, because neither the container 2 nor the main body lid 41 are applied on the mass sensor 100 as a load, a measured value is less than the initial value. Thus in a case of the measured value being less than the initial value, the control board 423 makes the indicator part 51 indicate "– (minus)."

Here will be described an operation in an automatic mode as one example of the operation of the automatic urine collection apparatus 1.

Firstly, if the patient M excretes urine, its moisture is detected by the urine sensor S1, a signal thereof is transmitted to the main body 3. If the control board 423 in the main body 3 receives the signal from the sensor S1, the board 23 drives the suction pump 53 for a predetermined time.

Then by driving the suction pump 53, air within the collection container 2 is sucked through the suction inlet 23b of the container lid 23, the air flow passage 414 of the main body lid 41, and a communication pipe not shown, the inside of the collection container 2 is adapted to be reduced in pressure.

Then the inside of the collection container 2 is reduced in pressure, and thereby the urine is sucked and collected in the container 2 from the urine receiver R through the tube T, the urine flow passage 413 of the main body lid 41, and the suction inlet 23b of the container lid 23.

Then if a predetermined time elapses after the suction pump 53 starts an operation, the control board 423 stops the pump 53.

In a state of the urine being accumulated in the collection container 2, the control board 423 subtracts the initial value from a value measured by the mass sensor 100 and calculates a mass of the urine. Next, by multiplying the mass of the urine by a predetermined coefficient (for example, relative density of urine of an average adult), a volume of the urine is calculated. Then the control board 423 makes the indicator part 51 indicate the calculated volume of the urine.

Here, in such a case for purpose of simply disposing of urine, it is not always requested to strictly fix the predetermined coefficient; for example, there is no problem in calculating a volume of the urine, assuming that a relative density of the urine is equivalent to that of water. On the other hand, When it is requested to accurately obtain data for purpose of such an inspection, it is preferable to fix the predetermined coefficient as properly as possible.

Moreover, the control board 423 determines a calculated urine volume.

As a result of the determination of the urine volume, if the control board 423 determines that the collection container 2 is near a full level (for example, not less than 60% of the effective volume of the container 2), the board 423 arouses attention for a user by performing a control of making the lamp of the indicator part 51 flicker.

As a result of the determination of the urine volume, if the control board 423 determines that the collection container 2 is the full level (for example, the effective volume of the container 2), the board 423 performs a control of making an alarm means 518 in FIG. 4 sound an alarm while transmitting a stop signal to the suction pump 53.

In addition, the controls of the automatic urine collection apparatus 1 by the control board 423 are not limited to the automatic mode. For example, using a known technology, it is possible to easily perform controls corresponding to the modes and the lamps indicated in the indicator part 51 shown in FIG. 4. Here will be described other controls performed by the control board 423, citing examples.

For example, the control board 423 can drive the suction pump 53 according to a signal of such the manual mode drive switch 517 from the operation panel 51a.

Furthermore, when not receiving a signal from the urine sensor S1 for a predetermined time, the control board 423 can intermittently operate the suction pump 53. Thus configured, it is possible to ventilate an inside of the urine receiver R, remove humidity thereof, and make a user comfortable. Specifically, for example, the suction pump 53 is automatically controlled for ten seconds every 15 to 60 minutes.

Furthermore, in a case of operating the suction pump 53 by the manual operation, the control board 423 stops the operation of the pump 53 after an elapse of a predetermined time. Thus configured, it is possible to prevent an excessive operation of the suction pump 53 and to protect it.

Thus although the present invention has been described, it is not limited to the embodiment and can be embodied in various modes.

In the embodiment, although the tank cover 44 is placed as an opening-closing type through a hinge part not shown, the present invention is not limited thereto; for example, a slide-housing type of the cover 44 is also available such that is stored inside the main body 3 in no use and is slid in use.

What is claimed is:

1. An automatic urine collection apparatus comprising:
   a collection container configured to accumulate urine transferred from a urine receiver through a tube; and
   a main body configured to support the collection container; said main body comprising:
   a suction pump configured to suck the urine received by the urine receiver and to carry the urine to the collection container;
   a container support part having a semi-cylindrical accommodation concave portion configured to accommodate the collection container;
   a mass sensor configured to include a sensor portion and to measure a mass of the collection container placed at a bottom part of the main body, the sensor portion being provided at the bottom part so as to be exposed upward from a hole formed in the bottom part;
   a control board configured to perform a calculation processing and calculate a volume of the urine based on a signal of the mass sensor; and
   an indicator configured to indicate the calculated volume of the urine.

2. The automatic urine collection apparatus according to claim 1, wherein the main body further comprises:
   a main body lid part configured to include a urine flow passage and an air flow passage, to be freely rotatably mounted on a shaft formed on a back face side, and to be openable and closeable;
   the tube configured to be connected to the collection container through the main body lid part and an introduction pipe; and
   a tube cover mounted on an upper portion of the main body lid part to cover the tube and fix the tube near the rotation shaft.

3. The automatic urine collection apparatus according to claim 1, wherein a vertical wall part which is a sidewall of the accommodation concave portion is formed along a shape of a side face of the collection container, and a gap is provided between the collection container and the vertical wall part so that the collection container and the vertical wall do not directly contact each other.

4. The automatic urine collection apparatus according to claim 1, wherein of the collection container is constructed of any one of transparent plastic or a and translucent plastic whereby a volume of the urine accumulated in the collection container is visible.

5. The automatic urine collection apparatus according to claim 1, wherein the collection container comprises:
   an approximately cylindrical tank part having a bottom and a predetermined depth;
   an opening formed in an upper face part on a top of the tank part and formed so as to be smaller than a diameter of the tank part; and
   a handgrip formed on a side face of the tank part.

6. The automatic urine collection apparatus according to claim 1, wherein the indicator indicates a volume of the urine by level display, and indicates a case of the collection container being not accommodated in the main body and a case of the volume of the urine nearing a full level.

7. The automatic urine collection apparatus according to claim 1, which further comprises:
   a urine sensor provided in the urine receiver which detects urine excreted from a patient, and wherein when the urine is detected, the automatic urine collection apparatus drives the suction pump and sucks the urine from the urine receiver into the collection container, and wherein when the urine is not detected for a predetermined time, the automatic urine collection apparatus repeats an intermittent operation of the suction pump, and ventilates an inside of the urine receiver.

8. The automatic urine collection apparatus according to claim 2, wherein the main body lid part is free-turnably supported with the main body by a hollow rotation shaft communicating with the suction pump, and wherein the urine flow passage and the air flow passage communicate with an inside of the collection container in conjunction with the main body lid part being coupled with the collection container.

9. The automatic urine collection apparatus according to claim 2, which further includes a container lid configured to close the opening of the tank part, said container lid comprising:

a suction inlet configured to communicate with the urine flow passage;

an introduction inlet configured to communicate with the urine flow passage; and a scattering prevention member configured to be hung down from an underside of the container lid between the suction inlet and the introduction inlet and constructed so as to block off a space between the introduction inlet and a urine surface of the tank part.

10. The automatic urine collection apparatus according to claim 9, wherein the urine flow passage and the air flow passage in the main body lid part, the introduction inlet and the suction inlet in the container lid are coupled by a container lid coupling mechanism interposed between the main body lid part and the container lid, and wherein the container lid coupling mechanism comprises a shaft disc fixed at a middle of the main body lid part from an underslide thereof, a turning body configured to fit outside the shaft disc and to be screwed by the container lid, a turning body support part free-slidably fitted in by the turning body, and a lever configured to turn the turning body and to couple the container lid with the main body lid part.

11. The automatic urine collection apparatus according to claim 9, which further includes a rubber member provided at connection ends of the urine flow passage and the air flow passage and configured to be closely connected to the introduction inlet and the suction inlet of the container lid when the main body lid part is coupled with the container lid.

* * * * *